United States Patent
Park et al.

(10) Patent No.: US 11,202,493 B2
(45) Date of Patent: Dec. 21, 2021

(54) ASYMMETRICAL STRUCTURE MOISTURIZING MASK PACK

(71) Applicant: GLO-ONE CO., LTD, Sejong (KR)

(72) Inventors: Joong Soon Park, Cheonan-si (KR); Hyo Deog Seo, Chungcheongnam-do (KR)

(73) Assignee: GLO-ONE CO., LTD., Sejong (KR)

(*) Notice: Subject to any disclaimer, the term of this patent is extended or adjusted under 35 U.S.C. 154(b) by 97 days.

(21) Appl. No.: 16/618,007

(22) PCT Filed: Dec. 4, 2017

(86) PCT No.: PCT/KR2017/014109
§ 371 (c)(1),
(2) Date: Nov. 27, 2019

(87) PCT Pub. No.: WO2018/236010
PCT Pub. Date: Dec. 27, 2018

(65) Prior Publication Data
US 2020/0170381 A1 Jun. 4, 2020

(30) Foreign Application Priority Data

Jun. 23, 2017 (KR) .................. 10-2017-0079479
Dec. 4, 2017 (KR) .................. 10-2017-0165301

(51) Int. Cl.
| | | |
|---|---|---|
| A45D 44/00 | (2006.01) |
| A61K 8/02 | (2006.01) |
| A61K 8/81 | (2006.01) |
| A61Q 19/00 | (2006.01) |
| B01D 67/00 | (2006.01) |
| B01D 71/38 | (2006.01) |
| B01D 71/48 | (2006.01) |

(52) U.S. Cl.
CPC .......... *A45D 44/002* (2013.01); *A61K 8/0212* (2013.01); *A61K 8/8129* (2013.01); *A61Q 19/00* (2013.01); *B01D 67/009* (2013.01); *B01D 67/0023* (2013.01); *B01D 67/0093* (2013.01); *B01D 71/38* (2013.01); *B01D 71/48* (2013.01); *A61K 2800/805* (2013.01); *A61K 2800/87* (2013.01); *B01D 2323/02* (2013.01); *B01D 2323/35* (2013.01); *B01D 2323/39* (2013.01); *B01D 2325/02* (2013.01); *B01D 2325/36* (2013.01)

(58) Field of Classification Search
CPC ...... A45D 44/002; A45D 44/22; A45D 44/00; A61Q 19/00; A61K 2800/805; A61K 2800/87; A61K 8/0212; A61K 8/8129; A61K 8/02; A61K 8/8147; A61K 36/53; A61K 8/042; D01D 5/0007
See application file for complete search history.

(56) References Cited

U.S. PATENT DOCUMENTS 8,512,612 B2    8/2013  Kook et al.

FOREIGN PATENT DOCUMENTS

| KR | 2001-0034995 | * | 5/2001 | ............. B01D 71/00 |
| KR | 10-0356044 B1 | | 10/2002 | |
| KR | 10-2011-0080066 | * | 7/2011 | ............. D04H 13/00 |
| KR | 10-2011-0080066 A | | 7/2011 | |
| KR | 10-2012-0021734 A | | 3/2012 | |
| KR | 10-2012-0078146 | * | 7/2012 | ............. B01D 69/10 |
| KR | 10-1198646 B1 | | 11/2012 | |
| KR | 10-2014-0033997 | * | 3/2014 | ............. A61L 27/56 |
| KR | 10-2014-0033997 A | | 3/2014 | |
| KR | 10-1623779 B1 | | 5/2016 | |

OTHER PUBLICATIONS

KR 10-2011-0080066 translation, Jul. 2011. (Year: 2011).*
KR 10-2014-0033997 translation, Mar. 2014. (Year: 2014).*
KR 10-2012-0078146 translation, Jul. 2012. (Year: 2012).*
KR 2001-0034995 translation, May 2001. (Year: 2001).*

* cited by examiner

*Primary Examiner* — Audrea B Coniglio
(74) *Attorney, Agent, or Firm* — Rabin & Berdo, P.C.

(57) ABSTRACT

The present invention relates to an asymmetric structure moisturizing mask pack comprising a polylactide. More specifically, the present invention relates to a porous membrane mask pack prepared from copolymers of polylactide and polyvinyl alcohol, wherein the skin contact surface of the mask pack is hydrophilic and the back surface thereof is hydrophobic.

2 Claims, 4 Drawing Sheets

ASYMMETRICAL STRUCTURE MOISTURIZING MASK PACK

TECHNICAL FIELD

The present invention relates to an asymmetrically structured moisturizing mask pack, and more particularly to a porous membrane mask pack prepared by copolymerizing polylactide with polyvinyl alcohol, wherein a skin contact surface of the mask pack is hydrophilic and a back surface thereof is hydrophobic.

BACKGROUND ART

Skin, which is the organ that covers the exterior of the body, is an important tissue having biochemical and physical functions that protect the human body from the external environment.

However, recently, skin damage caused by severe air pollution and UV exposure has emerged as a serious problem. In particular, the skin on the face is exposed to the external environment the most, and skin care such as UV blocking, waste removal and skin moisturizing is very important. Excessive cleaning makes the skin dry and rough, and in particular, sensitive skin entails concerns of inflammation due to hypersensitivity, acne or atopic dermatitis due to inhibited epidermal cell formation.

In order to solve this problem, a mask pack has been developed as a tool for nourishing facial skin. A pack is a cosmetic containing active ingredients for supplying the moisture and cosmetic ingredients to the skin by covering a rough or tired face, and removing effectively the waste accumulated in the skin and restoring physiological functions Generally, the cosmetic mask pack is prepared by adding a cosmetic composition to a nonwoven fabric. However, when the nonwoven fabric has a cosmetic composition added thereto, it becomes stiff and thus has a bad texture since it is a synthetic polymer. In addition, when the nonwoven fabric is used in the state of being soaked in the cosmetic composition, it may be exposed to air, thus resulting in degeneration of the cosmetic composition, low adhesion to the skin, and high possibility of occurrence of skin irritation due to contact of a high concentration of the cosmetic composition with the skin.

In order to overcome the drawbacks of the nonwoven mask pack, research and development on a gel-type mask pack has been actively conducted. However, the gel mask of the prior art is generally used in addition to synthetic resins, non-woven fabrics, meshes or nets because hydrogel alone cannot maintain the desired shape thereof. However, hydrogels were often peeled (detached) from nonwoven fabrics and hydrogels using synthetic resins were controversial in terms of biocompatibility and stability. In addition, there is a controversy over moisturizing efficacy of the nonwoven mask pack and the hydrogel mask pack due to evaporation upon exposure to air.

Accordingly, the present inventors developed a moisturizing mask pack having an asymmetric structure, wherein a skin contact surface of the mask pack utilizes polylactide as a biocompatible material and is thus hydrophilic, and a back surface of the mask pack is hydrophobic, thus completing the present invention.

Claim 1 of the prior patent, Korean Patent No. 10-1623779, entitled "Mesh comprising naturally derived ingredients and hydrogel mask using support" discloses a mesh for a support of a hydrogel mask comprising a naturally derived ingredient, wherein the mesh is woven with a mixture of 1 to 20% by weight of at least one fiber selected from the group consisting of natural cellulose extracted from conifers (soft wood pulp), Tencel as a cellulose-regenerated fiber, and viscose rayon as a cellulose-regenerated fiber, and 80 to 99% by weight of a natural corn fiber (PLA fiber).

DISCLOSURE

Technical Problem

Therefore, the present invention has been made in view of the above problems, and it is one object of the present invention to provide an asymmetrically structured moisturizing mask pack, and more particularly to provide a porous membrane mask pack prepared by copolymerizing polylactide with polyvinyl alcohol, wherein a skin contact surface of the mask pack is hydrophilic and a back surface thereof is hydrophobic.

It is another object of the present invention to provide an asymmetrically structured moisturizing mask pack that is produced in the form of a porous membrane and can thus promote adhesion to the skin and absorption of nutrients.

Technical Solution

In accordance with an aspect of the present invention, the above and other objects can be accomplished by the provision of an asymmetrically structured mask pack including a porous membrane having one surface that is hydrophobic, and another surface that is hydrophilic, wherein the hydrophilic surface is hydrophilized by plasma surface treatment or treatment with alkaline solution.

A material for the porous membrane may be a copolymer of polylactide with polyvinyl alcohol.

Porosity of the porous membrane may be formed by salt-leaching phase transition.

In accordance with another aspect of the present invention, there is provided a method for producing an asymmetrically structured mask pack including a first step of copolymerizing polylactide with polyvinyl alcohol, a second step of producing the copolymerized polylactide and polyvinyl alcohol into a microfiber sheet by electrospinning, a third step of producing a porous membrane from the microfiber sheet by salt-leaching phase transition, and a fourth step of hydrophilizing one surface of the porous membrane by plasma surface treatment or treatment with alkaline solution.

The porous membrane may have one surface that is hydrophilic and has a porosity (v/v) of 90 to 95% and another surface that is hydrophobic and has a porosity (v/v) of 5 to 10% to suppress evaporation of moisture.

The porous membrane may be hydrophilized through treatment with a 5 to 20% (w/v) NaOH solution for 5 to 20 minutes.

Advantageous Effects

The present invention provides an asymmetrically structured moisturizing mask pack containing polylactide, and more particularly provides a porous membrane mask pack prepared by copolymerizing polylactide with polyvinyl alcohol, wherein a skin contact surface of the mask pack is hydrophilic and a back surface thereof is hydrophobic.

The present invention is directed to an asymmetrically structured moisturizing mask pack that promotes the absorption of the mask pack composition in the skin, which is developed as a new material that can be applied to cosmetics and thus has a wide range of industrial applications.

BEST MODE

Figure 1:
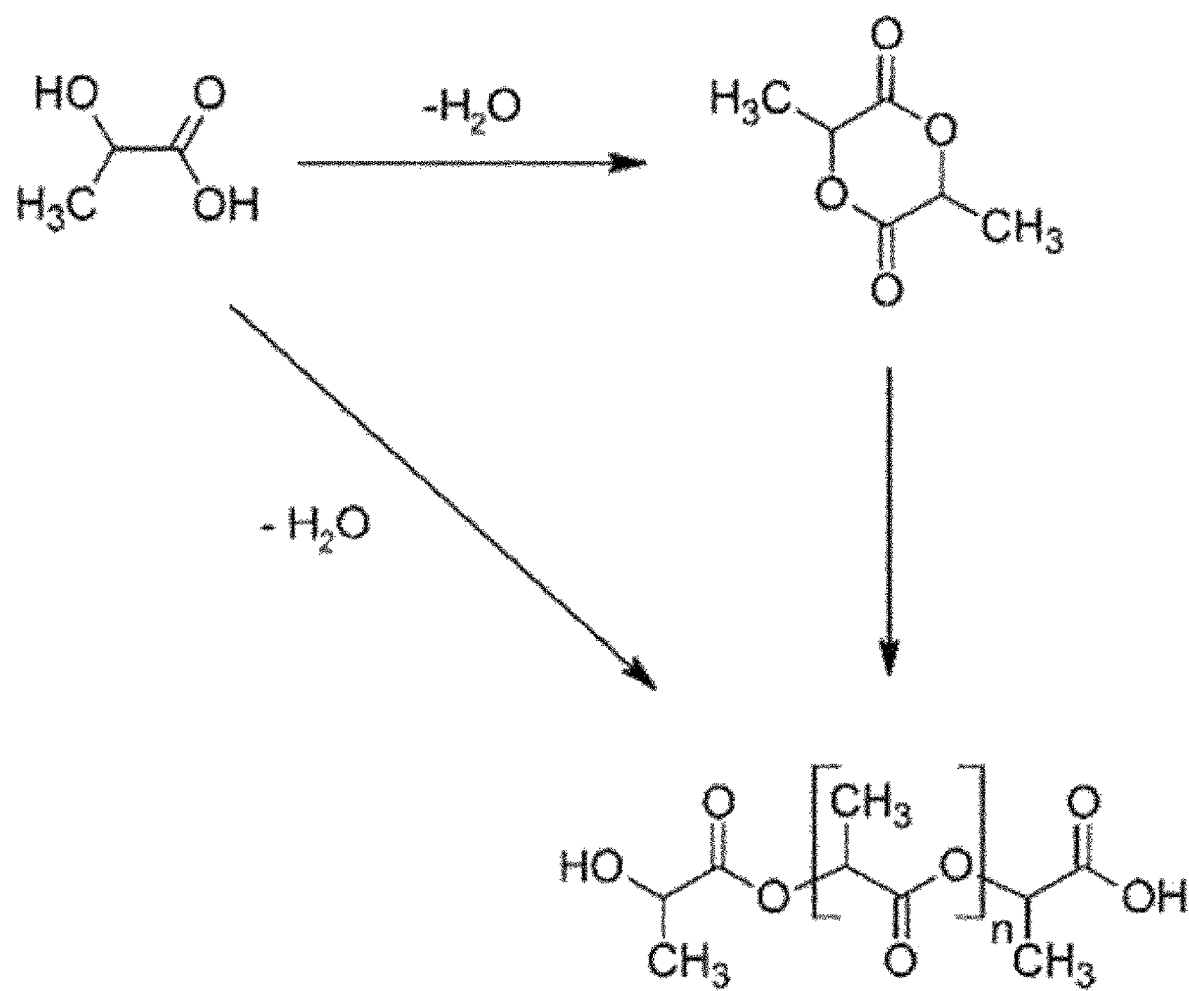
FIG. 1 shows polylactide which is a biocompatible material.

The terms or words used in the present specification and claims should be construed, not as having ordinary or dictionary meanings, but as having meanings and concepts that are consistent with the technical ideas of the present invention, based on the principle that an inventor can appropriately define the concept of a term in order to describe the invention in the best way.

Therefore, it should be understood that the configurations shown in the embodiments and drawings described in the present specification are suggested only as the most preferred embodiments of the present invention and do not represent all of the technical ideas of the present invention, and various equivalents and modifications thereof that can replace them at the time of the present application are possible.

Example 1. Production of an Asymmetrically Structured Moisturizing Mask Pack Using Polylactide

1) First Step of Producing Sheet by Copolymerizing Polylactide with Polyvinyl Alcohol Polylactide, known as a biocompatible material, has been used as a plate, screw and suture for bone fractures for more than 30 years, and is known to be decomposed into water and carbon dioxide in the human body. In particular, since the injection of polylactide particles into the skin is known to promote collagen formation, polylactide has been developed as a medical device in the US and imported into Korea. However, polylactide has considerably different rates of decomposition depending on the molecular weight thereof, and enantiomers thereof are present, and among them, a commonly used polyisomer is poly-L-lactide having crystallinity.

In the present example, a polylactide, which is a biocompatible material, is copolymerized with polyvinyl alcohol, which is hydrophilic, to prepare an asymmetrically structured moisturizing mask pack in the form of a porous membrane. A mask pack is produced, which can be mass-produced and has fine pores, using electrospinning and salt-leaching phase transition methods.

2) Second Step of Producing Copolymerized Polylactide and Polyvinyl Alcohol into Microfiber Sheet by Electrospinning Electrospinning is a process for producing ultrafine fibers on a nanometer scale. Unlike conventional methods that depend on physical forces, materials considered unsuitable for production into fibers can be produced into fibers because of the use of electrical repulsive forces in the fiber-forming process and a non-woven fabric can be produced even with a small amount of materials.

In addition, factors affecting the thickness of the fibers by electrospinning include the concentration of the solution, the applied voltage, the distance between the electrodes (tip-to-collector distance, TCD), flow rate, temperature and humidity. In general, since the concentration of the solution is proportional to the viscosity thereof, as the concentration increases under a certain voltage, the bending and stretching forces decrease and thus the diameter of the fiber increases. In addition, as the applied voltage increases, whipping instability increases and the diameter of the fiber decreases, but the minimum diameter is obtained at a certain distance.

Electrospinning is advantageously capable of producing very thin fibers, is applicable to a very wide range of polymers and can be realized by a simple device and a simple spinning process. Preferably, adhesion of the skin contact surface of the mask pack sheet is increased by controlling the thickness of the fiber through electrospinning.

In order to further upgrade the performance of conventional cosmetic mask pack sheets, sheets are made with copolymers of polylactide and polyvinyl alcohol by electrospinning, thereby producing sheets from the microfiber fibers.

Accordingly, it is possible to promote adhesion ability to the skin and moisture content, and improve the absorption rate of the essence into the skin. In addition, it is possible to adsorb fine dust and sebum on the fiber tissue due to excellent skin adhesion and thereby effectively remove waste matter.

3) Third Step of Producing Porous Membrane from Microfiber Sheet by Salt-Leaching Phase Transition Method In term of 'phase transition', 'phase' means a part of a substance in a certain state that exhibits the same physical and chemical properties. That is, a phase refers to a homogeneous part of a substance, which may be a single substance or a mixture. Even in case of a mixture, it is said that a single phase is formed if it is mixed completely and homogeneously. In term of 'phase transition', 'transition' means transferring or relocation from one place to another.

In other words, phase transition means that any phase, which is a homogeneous part of a substance, changes to another phase due to a change in variables such as temperature, pressure, magnetic field, composition, and is also called "phase transformation".

In addition, when a substance is in one phase, it can undergo partial phase transition due to a change in variables and can thus be separated into two phases, which is called "phase separation". That is, phase separation is a phenomenon caused by phase transition.

Methods for producing membranes using phase transition, phase transformation or phase separation include non-solvent induced phase separation (NIPS), thermally induced phase separation (TIPS), solvent evaporation precipitation, vapor phase precipitation and evaporation control precipitation, depending on the phase separation principle.

Non-solvent induced phase separation, which is also called immersion precipitation or solvent exchange, is a method that is suitable for mass production due to relatively simple and inexpensive production process. In the non-solvent induced phase separation process, a polymer to be used as a raw material is dissolved in a suitable solvent to prepare a thermodynamically stable polymer solution, cast into a flat-plate, tube or hollow fiber form, and then immersed in a non-solvent. This causes phase separation of the polymer, so that a portion of the region occupied by the solvent and the non-solvent becomes pores, thereby producing a porous membrane.

The surface of the microfiber sheet is prepared by the salt-leaching phase transition method, and the surface in contact with the skin has a porosity of 90% or more and is hydrophilic, whereas the back surface a porosity of less than 10% and is hydrophobic. When the mask pack is attached to the skin, moisture is absorbed into the pores in the skin, so that skin moisturization is promoted and the composition penetrates well into the skin, thereby increasing efficacy thereof.

Figure 2:
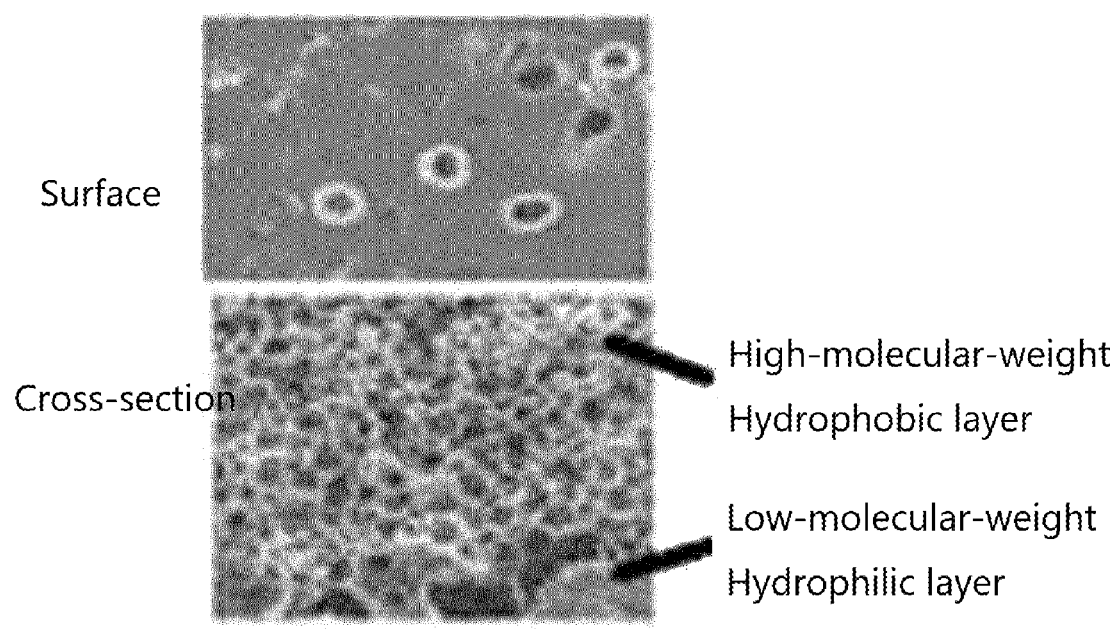
FIG. 2 shows a surface structure and a cross-sectional structure of an asymmetrically structured moisturizing mask pack.
Figure 3:
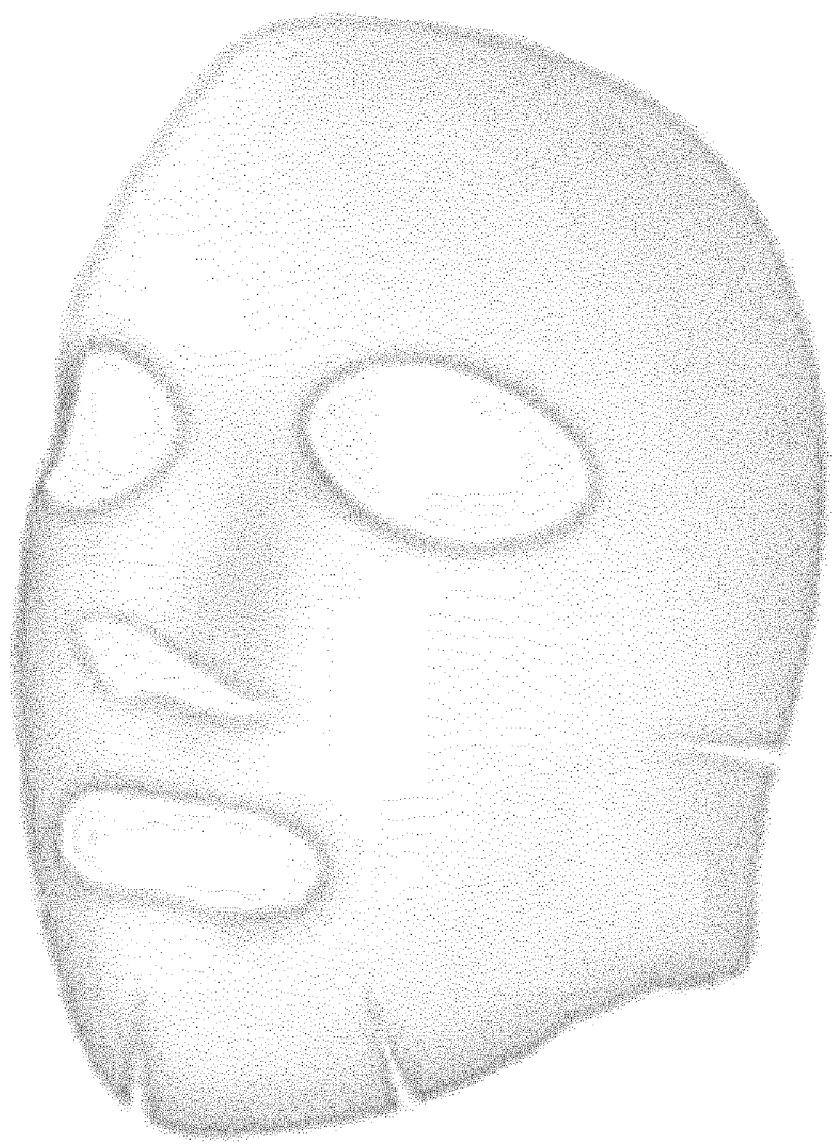
FIG. 3 shows a conventional silicon hydrogel mask pack.
Figure 4:
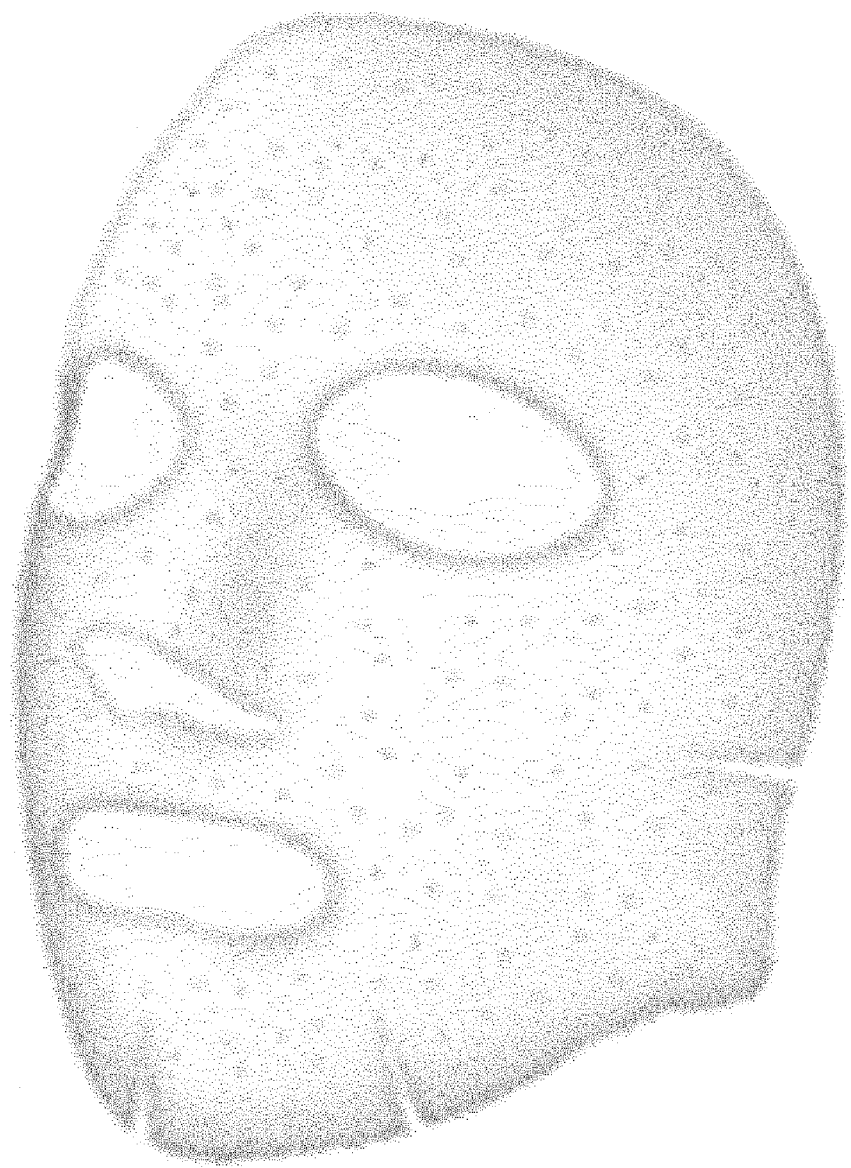
FIG. 4 shows an asymmetrically structured moisturizing mask pack containing polylactide.

FIG. 2 shows a surface structure and a cross-sectional structure of the asymmetrically structured moisturizing mask pack. FIG. 2 shows a hydrophobic surface and a hydrophilic cross-sectional surface in the asymmetric structure produced by the phase transition method.

In particular, when the mask pack is attached to the skin, the temperature of the substance contained in the pack is increased and thus the composition of the mask pack promotes skin absorption, and evaporation to the atmosphere is suppressed due to the hydrophobic surface.

Through the phase transition method, a porous membrane having a porosity (v/v) of 90 to 95% on a skin adhesion surface and a porosity (v/v) of about 5 to 10% on a back surface is produced to thus suppress evaporation of the mask pack composition into the atmosphere and promote absorption thereof into the skin.

4) Fourth Step of Hydrophilizing One Surface of Porous Membrane by Plasma Surface Treatment or Treatment with Alkaline Solution Most polymers, such as polyethylene and polypropylene, are hydrophobic due to the nonpolar molecular structure thereof. Therefore, these polymers can inhibit the absorption of the mask pack composition on the surface that is in contact with the skin.

Accordingly, the present inventors hydrophilized one surface of the porous membrane through plasma treatment, so that the mask pack composition may be contained in the skin contact surface to thus enhance absorption in the skin.

Preferably, the skin contact surface is hydrophilized through plasma surface treatment using plasma chemical vapor deposition. As a result, the hydrophilicity of the skin contact surface can be increased by plasma treatment, and the hydrophobicity of the back surface can suppress microbial growth and evaporation of the mask pack composition.

In addition, treatment with alkaline solution can be performed in order to hydrophilize the porous membrane. Preferably, the porous membrane is hydrophilized with 10% (w/v) NaOH for 20 minutes.

Experimental Example 1. Hydrophilization of an Asymmetrically Structured Mask Pack Containing Polylactide Experimental Example 1 relates to a hydrophilization process of an asymmetrically structured mask pack containing polylactic acid (PLA) prepared in the above Example.
1) A PLA membrane and a PLGA (polylactic-co-glycolic acid) membrane (20 mm 30 mm) were prepared.
2) 5, 10, 20, 30, 40 and 50% (w/v) NaOH solutions were prepared.
3) 20 ml of each NaOH solution was added to a petri dish and a sheet cross-sectional surface was subjected to hydrophilization.
4) One surface of each of the PLA membrane and the PLGA membrane was immersed in the NaOH solution to make the membrane hydrophilic.
5) The membrane was measured for 1 hour at an interval of 10 minutes.

As a result, it was found that the PLA membrane is preferably hydrophilized with 10% NaOH for 20 minutes and the PLGA membrane is preferably hydrophilized with 20% NaOH for 10 minutes.

Experimental Example 2. Preparation of Mask Pack Composition

A mask pack composition was prepared from ingredients including a herbal extract, a solvent, a wetting agent, a viscosity modifier, a surfactant, a skin-conditioning agent, a preservative, a thickener, a pH adjuster, a flavoring agent and a chelating agent. The contents thereof are determined so that they can be easily utilized by those skilled in the art to prepare a pack composition.

TABLE 1

| | Mask pack sheet |
|---|---|
| Sample 1 | Asymmetrically structured moisturizing mask pack containing polylactide produced in Example 1 |
| Sample 2 | PLA non-woven sheet |
| Sample 3 | PLGA membrane sheet |
| Sample 4 | Commercially available mask pack sheet |

Example 3. Sensory Evaluation of Moisturizing Satisfaction and Skin Stability

A sensory test based on a 9-point scale (1-9) was performed for moisturizing satisfaction, skin stability and texture according to the mask pack sheet produced from the same mask pack composition. The panel included 20 male adults and 20 female adults in 20s to 30s. The results of the test are shown in the following [Table 2]. The higher the number, the better the effect.

TABLE 2

| | Moisturizing satisfaction | Skin stability | Texture | Overall evaluation |
|---|---|---|---|---|
| Sample 1 | 8.5 | 7.9 | 8.0 | 8.3 |
| Sample 2 | 4.3 | 5.6 | 4.2 | 4.7 |
| Sample 3 | 5.5 | 4.3 | 5.6 | 5.3 |
| Sample 4 | 2.3 | 3.1 | 2.0 | 2.4 |

As can be seen from [Table 2], the overall moisturizing effect of the asymmetrically structured moisturizing mask pack containing polylactide is the highest.

Experimental Example 4. Evaluation of Moisture Retention Capacity

Five test subjects evaluated the moisture retention capacity of each sheet produced in Experiment Example 1 as follows. The moisture retention capacity was obtained by measuring the electrical conductivity of the skin surface using SKICON-200. After attaching the mask pack to the skin (16 cm²) for 30 minutes in a constant-temperature constant-humidity room maintained at 25° C. and 40% relative humidity, the mask pack was removed therefrom and the resistance value (moisture loss) was measured over time.

TABLE 3

|  |  | Sample 1 | Sample 2 | sample 3 | sample 4 |
|---|---|---|---|---|---|
| Short-term moisturizing | One hour after removal | 820 | 650 | 520 | 300 |
| Long-term moisturizing | Used once for five days | 30 | 5.3 | 26 | 5.8 |

As can be seen from the above [Table 3], the overall moisture retention capacity of the asymmetrically structured moisturizing mask pack containing polylactide is the highest.

The invention claimed is:

1. An asymmetrically structured mask pack for nourishing facial skin comprising a porous membrane having one surface that is hydrophobic, and another surface that is hydrophilic, wherein the hydrophilic surface is hydrophilized by treatment with alkaline solution, wherein a material for the porous membrane is a copolymer of polylactide with polyvinyl alcohol, wherein porosity of the porous membrane is formed by salt-leaching phase transition so that the hydrophilic surface has a porosity (v/v) of 90 to 95% and the hydrophobic surface has a porosity (v/v) of 5 to 10% to suppress evaporation of moisture.

2. A method for producing an asymmetrically structured mask pack for nourishing facial skin, comprising:

a first step of copolymerizing polylactide with polyvinyl alcohol;

a second step of producing a microfiber sheet with copolymers of polylactide and polyvinyl alcohol by electrospinning;

a third step of producing a porous membrane from the microfiber sheet by salt-leaching phase transition; and a fourth step of hydrophilizing one surface of the porous membrane by treatment with a 5 to 20% (w/v) NaOH solution for 5 to 20 minutes, wherein the one surface, which is hydrophilic, of the porous membrane has a porosity (v/v) of 90 to 95% and another surface, which is hydrophobic, has a porosity (v/v) of 5 to 10% to suppress evaporation of moisture.

* * * * *